United States Patent [19]

Satzinger et al.

[11] 4,284,632
[45] Aug. 18, 1981

[54] 3-PYRROLIN-2-ONE DERIVATIVES AND COMPOSITIONS

[75] Inventors: Gerhard Satzinger, Denzlingen; Manfred F. Herrmann, St. Peter; Gustav Hechtfischer, Freiburg, all of Fed. Rep. of Germany

[73] Assignee: Warner-Lambert Company, Morris Plains, N.J.

[21] Appl. No.: 75,479

[22] Filed: Sep. 14, 1979

Related U.S. Application Data

[60] Division of Ser. No. 922,018, Jul. 5, 1978, Pat. No. 4,205,078, which is a continuation of Ser. No. 821,259, Aug. 3, 1977, abandoned.

[30] Foreign Application Priority Data

Aug. 14, 1976 [DE]  Fed. Rep. of Germany ....... 2636723

[51] Int. Cl.$^3$ ................... A61K 31/535; A61K 31/54; C07D 413/12; C07D 417/12

[52] U.S. Cl. ................... 424/246; 424/248.57; 424/250; 424/263; 424/267; 548/300; 548/146; 260/244.4; 260/245.7; 260/326.5 D; 260/326.5 FL; 424/270; 424/272; 424/273 R; 424/274; 544/58.5; 544/58.6; 544/58.7; 544/131; 544/141; 544/360; 544/372; 542/434; 542/436; 546/194; 546/208; 546/281; 548/181; 548/214; 548/215; 548/240

[58] Field of Search ............ 544/131, 141, 58.6, 544/58.7, 58.5, 360, 372; 546/194, 208, 281; 548/300, 181, 214, 215, 240; 260/244.4, 245.7, 326.5 D, 326.5 FL; 424/248.54, 246, 250, 263, 267, 273 R, 274, 270, 272; 542/434, 436

[56] References Cited

PUBLICATIONS

Kurkovskaya et al., "Chem. Abstracts" vol. 83 (1975) No. 96135k.

Primary Examiner—Henry R. Jiles
Assistant Examiner—R. W. Ramsuer
Attorney, Agent, or Firm—Stephen I. Miller

[57] ABSTRACT

New 3-cyclicaminoalkoxy-4-phenyl-3-pyrrolin-2-ones are disclosed. These compounds exhibit anti-hypertensive and vasodilatory action.

8 Claims, No Drawings

3-PYRROLIN-2-ONE DERIVATIVES AND COMPOSITIONS

This is a divisional of U.S. Ser. No. 922,018, filed July 5, 1978, now U.S. Pat. No. 4,205,078, which is a continuation of U.S. Ser. No. 821,259, filed Aug. 3, 1977, which is now abandoned.

The new and novel 3-pyrrolin-2-one derivatives according to the present invention are compounds of the formula:

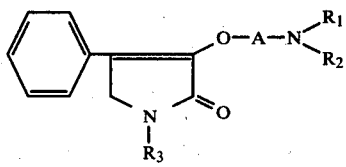

wherein $R_1$ and $R_2$, which may be the same or different, are straight-chain or branched alkyl radicals containing up to 3 carbon atoms or, together with the nitrogen atom to which they are attached, can form a 5-, 6- or 7-membered ring which can contain a further nitrogen atom or an oxygen or sulphur atom, A is a straight or branched hydrocarbon chain containing 2 to 4 carbon atoms and $R_3$ is a saturated or unsaturated, straight or branched aliphatic hydrocarbon radical containing up to 6 carbon atoms or is an -Alk-Ar radical, in which Alk is an alkylene chain containing up to 3 carbon atoms and Ar is a phenyl or heteroaryl radical optionally substituted by halogen atoms and/or lower alkoxy radicals; and the pharmacologically compatible salts thereof with inorganic and organic acids.

We have found that the compounds of formula (I) possess valuable pharmacological properties and, in particular, exhibit an anti-hypertensive and vasodilatory action. Thus, they represent a new class of compounds for the potential therapy of various forms of high blood pressure and of angiopathies.

Heterocyclic rings within the meaning of the present invention are saturated nitrogen heterocycles, for example, the pyrrolidine, imidazolidine, piperidine, piperazine and hexahydroazepin rings, or mixed heterocycles, for example, the morpholine, thiomorpholine, oxazolidine or thiazolidine rings, the pyrrolidine, piperidine, morpholine and piperazine rings being preferred.

Ar preferably means a phenyl, pyridyl or furyl radical optionally substituted by a chlorine atom or by an alkoxy radical containing up to 3 carbon atoms, the methoxy radical being preferred.

Alk is preferably a methylene, ethylene or ethylidene chain.

Those compounds of formula (I) are especially preferred in which $R_1$ and $R_2$ are methyl, ethyl or propyl radicals or, together with the nitrogen atom to which they are attached, represent a piperidino, morpholino, piperazino or $N_4'$-methylpiperazino radical, A is an ethylene or propylene chain, $R_3$ is a saturated or unsaturated alkyl radical containing up to 4 carbon atoms, Alk is a methylene, ethylene or ethylidene chain, and Ar is a phenyl, pyridyl or furyl ring optionally substituted by a chlorine atom or a methoxy radical.

A further preferred group of compounds are those in which $R_3$ is a butyl radical or a benzyl, picolyl, or furfuryl radical.

The new compounds according to the present invention can be prepared by reacting a compound of the general formula:

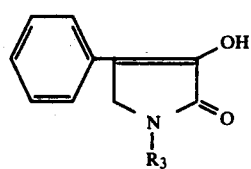

wherein $R_3$ has the same meaning as above, with a compound of the general formula:

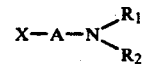

wherein $R_1$, $R_2$ and A have the same meanings as above and X is a halogen atom, preferably in the presence of an adjuvant base. The compound (I) thus obtained may be if desired, subsequently converted into a pharmacologically compatible salt.

The reaction of compounds (II) with compounds (III) is preferably carried out in a polar aprotic solvent, for example, dimethyl formamide, dimethyl sulphoxide or hexamethyl phosphoric acid triamide, since, in this manner, a product is obtained which is substantially free from by-products substituted in the 5-position. As adjuvant base, there can be used, for example, a tertiary amine or a suspension of sodium hydride in the solvent employed.

For economic and toxicological reasons, dimethyl formamide is preferred as being the most appropriate solvent.

The reaction is preferably carried out at a temperature of from about 60° to 100° C. but it is possible to go above or below this temperature range.

The compounds of general formula (I) can, for the purpose of purification and for galenical reasons, be converted into crystalline, pharmacologically compatible salts.

The salts can be prepared in the usual manner by neutralization of the bases with appropriate inorganic or organic acids. Such acids include, for example, hydrochloric acid, sulphuric acid, phosphoric acid, hydrobromic acid, acetic acid, tartaric acid, lactic acid, citric acid, malic acid, salicylic acid, ascorbic acid, malonic acid, maleic acid and succinic acid.

The compounds of general formula (II) can be prepared by a chemical novel process according to the process disclosed in U.S. Ser. No. 967,339, filed Dec. 7, 1978, now allowed.

The following examples are given for the purpose of illustrating the present invention:

EXAMPLE 1

1-Benzyl-3-(β-dimethylaminoethoxy)-4-phenyl-3-pyrrolin-2-one 22.0 g. 1-benzyl-3-hydroxy-4-phenyl-3-pyrrolin-2-one is introduced portionwise at 70°–80° C. into a suspension of 2.5 g. 80% sodium hydride in 400 ml. anhydrous dimethyl formamide. The reaction mixture is stirred for half an hour at this temperature, then cooled to ambient temperature and mixed with 15.0 g. β-dimethylaminoethyl chloride. Within the course of 25 minutes, the reaction mixture is brought to a temperature of 90° C. and maintained for 30–40 minutes. The bulk of the solvent is removed in a vacuum, the residue is partitioned between water and diethyl ether and the basic component is extracted from the ethereal phase by means of 2 N hydrochloric acid. There is obtained 15 g. (48% of theory) 1-benzyl-3-(β-dimethylaminoethoxy)-4-phenyl-3-pyrrolin-2-one hydrochloride; m.p. 61°–62° C., after recrystallization from cyclohexane.

In an analogous manner, there are obtained, by the reaction of 1-benzyl-3-hydroxy-4-phenyl-3-pyrrolin-2-one with:

(a) β-diethylaminoethyl chloride and neutralization of the free base obtained with fumaric acid in isopropanol, 21.0 g. (44% of theory) 1-benzyl-3-(β-diethylaminoethoxy)-4-phenyl-3-pyrrolin-2-one fumarate; m.p. 121°–122° C. (0.1 molar batch)

(b) γ-dimethylaminopropyl chloride at 110° C. and a reaction time of 75 minutes, after recrystallization from dioxan, 12.5 g. (26% of theory) 1-benzyl-3-(γ-dimethylaminopropoxy)-4-phenyl-3-pyrrolin-2-one; m.p. 145°–149° C. (0.1 molar batch).

(c) β-N-morpholinoethyl chloride, 16.0 g. (76% of theory) 1-benzyl-3-(β-N-morpholinoethoxy)-4-phenyl-3-pyrrolin-2-one; m.p. 100°–101° C., after recrystallization from cyclohexane (0.05 molar batch).

EXAMPLE 2

1-n-Butyl-3-(β-diethylaminoethoxy)-4-phenyl-3-pyrrolin-2-one 23.1 g.

1-n-butyl-3-hydroxy-4-phenyl-3-pyrrolin-2-one is reacted with 20.3 g. β-diethylaminoethyl chloride in a manner analogous to that described in Example 1. The 1-n-butyl-3-(β-diethylaminoethoxy)-4-phenyl-3-pyrrolin-2-one obtained in the form of the free base is reacted in diethyl ether with oxalic acid to give the crystalline oxalate. The yield is 24.2 g. (58% of theory); m.p. 120°–121° C., after recrystallization from methyl ethyl ketone.

In an analogous manner, there are obtained, by the reaction of 1-n-butyl-3-hydroxy-4-phenyl-3-pyrrolin-2-one with (a) dimethylaminoethyl chloride, 15.5 g. (40% of theory) 1-n-butyl-3-(β-dimethylaminoethoxy)-4-phenyl-3-pyrrolin-2-one; the crystalline oxalate is obtained by reaction with oxalic acid in ethyl acetate; m.p. 120°–122° C., after recrystallization from methyl ethyl ketone;

(b) $N_1$-β-chloroethyl-$N_4$-methylpiperazine, 1-n-butyl-3-[$N_1$-β-($N_4$-methyl)piperazinoethoxy]-4-phenyl-3-pyrrolin-2-one; dioxalate m.p. 199° C. 32.5 g. (0.14 mol) 1-n-butyl-3-hydroxy-4-phenyl-3-pyrrolin-2-one is added, with stirring, at 40° C. to a suspension of 4.2 g. sodium hydride (80%) in 200 ml. dimethyl formamide. When the evolution of hydrogen ceases, 30.0 g. $N_1$-β-chloroethyl-$N_4$-methylpiperazine is added and the mixture allowed to react for 30 minutes at 70° C. The mixture is immediately poured into 1.5 liters of ice water. This is then extracted twice with dichloromethane and the organic phase is washed with water. After drying over anhydrous magnesium sulphate, the solvent is distilled off. The residue (base) is taken up in diethyl ether and oxalic acid is added to precipitate out the di-oxalate. After recrystallization of this dioxalate from aqueous methanol, there is obtained 33.0 g. (44% of theory) of the desired end product.

EXAMPLE 3

1-Allyl-3-(β-dimethylaminoethoxy)-4-phenyl-3-pyrrolin-2-one

In a manner analogous to that described in Example 1, 30.6 g. 1-allyl-3-hydroxy-4-phenyl-3-pyrrolin-2-one are reacted with 23.0 g. β-dimethylaminoethyl chloride. The base obtained is reacted with gaseous hydrogen chloride in ethyl acetate. There is obtained 15.0 g. (45.5% of theory) 1-allyl-3-(β-dimethylaminoethoxy)-4-phenyl-3-pyrrolin-2-one hydrochloride: m.p. 115°–117° C., after recrystallization from methyl ethyl ketone.

EXAMPLE 4

1-Ethyl-3-(β-piperidinoethoxy)-4-phenyl-3-pyrrolin-2-one

In a manner analogous to that described in Example 1, 30.5 g. 1-ethyl-3-hydroxy-4-phenyl-3-pyrrolin-2-one is reacted with 21.5 g. β-piperidinoethyl chloride. The base obtained is converted into the crystalline hydrochloride in ethyl acetate by means of gaseous hydrogen chloride. There is obtained 22.5 g. (42% of theory) 1-ethyl-3-(β-piperidinoethoxy)-4-phenyl-3-pyrrolin-2-one hydrochloride; m.p. 120° C., (decomp.), after recrystallization from methyl ethyl ketone.

EXAMPLE 5

1-Furfuryl-3-(β-dimethylaminoethoxy)-4-phenyl-3-pyrrolin-2-one 25.5 g. 1-furfuryl-3-hydroxy-4-phenyl-3-pyrrolin-2-one is reacted with 20.0 g. β-dimethylaminoethyl chloride in a manner analogous to that described in Example 1. The base obtained is converted into the crystalline hydrochloride in diisopropyl ether by means of gaseous hydrogen chloride. There is obtained 7.5 g. (21% of theory) 1-furfuryl-3-(β-dimethylaminoethoxy)-4-phenyl-3-pyrrolin-2-one hydrochloride; m.p. 145°–148° C., after recrystallization from methyl ethyl ketone.

EXAMPLE 6

1-(3-Picolyl)-3-(β-dimethylaminoethoxy)-4-phenyl-3-pyrrolin-2-one

In a manner analogous to that described in Example 1, 26.6 g. 1-(3-picolyl)-3-hydroxy-4-phenyl-2-pyrrolin-2-one is reacted with 20.0 g. β-dimethylaminoethyl chloride. The base so obtained is converted into the crystalline oxalate in isopropanol and then recrystallized from methanol. There is obtained 20.4 g. (39% of theory) 1-(3-picolyl)-3-(β-dimethylaminoethoxy)-4-phenyl-3-pyrrolin-2-one oxalate; m.p. 160° C. (decomp.).

EXAMPLE 7

1-(1-Phenethyl)-3-(β-dimethylaminoethoxy)-4-phenyl-3-pyrrolin-2-one

In a manner analogous to that described in Example 1, 11.3 g. 1-(1-phenethyl)-3-hydroxy-4-phenyl-3-pyrrolin-2-one is reacted with 10.0 g. β-dimethylaminoethyl chloride. The base thus obtained is converted into the crystalline oxalate by reaction with oxalic acid in diethyl ether. There is obtained 3.3 g. (20% of theory) 1-(1-phenethyl)-3-(β-dimethylaminoethoxy)-4-phenyl-3-pyrrolin-2-one oxalate; m.p. 163°–165° C., after recrystallization from acetonitrile.

EXAMPLE 8

1-(4-Chlorobenzyl)-3-(β-diethylaminoethoxy)-4-phenyl-3-pyrrolin-2-one

In a manner analogous to that described in Example 1, 30.0 g. 1-(4-chlorobenzyl)-3-hydroxy-4-phenyl-3-pyrrolin-2-one is reacted with 20.3 g. β-diethylaminoethyl chloride. The base thus obtained is converted into the crystalline hydrochloride in ethyl acetate by means of gaseous hydrogen chloride. There is obtained 24.8 g. (57% of theory) 1-(4-chlorobenzyl)-3-(β-diethylaminoethoxy)-4-phenyl-3-pyrrolin-2-one hydrochloride; m.p. 143°–145° C., after recrystallization from methyl ethyl ketone.

EXAMPLE 9

1-(2-Phenethyl)-3-(β-dimethylaminoethoxy)-4-phenyl-3-pyrrolin-2-one

In a manner analogous to that described in Example 1, 33.5 g. 1-(2-phenethyl)-3-hydroxy-4-phenyl-3-pyrrolin-2-one is reacted with 30.0 g. β-dimethylaminoethyl chloride. The base so obtained is converted into the crystalline hydrochloride by reaction with gaseous hydrogen chloride in ethyl acetate. There is obtained 9.0 g. (19% of theory) 1-(2-phenethyl)-3-(β-dimethylaminoethoxy)-4-phenyl-3-pyrrolin-2-one hydrochloride; m.p. 135°–137° C., after recrystallization from methyl ethyl ketone.

EXAMPLE 10

1-(4'-Methoxybenzyl)-3-[$N_1$-β-($N_4$-methyl)-piperazinoethoxy]-4-phenyl-3-pyrrolin-2-one In a manner analogous to that described in Example 2b, 44.3 g. 1-(4'-methoxybenzyl)-3-hydroxy-4-phenyl-3-pyrrolin-2-one is reacted with 30.0 g. $N_1$-β-chloroethyl-$N_4$-methyl-piperazine. The free base, which melts at 101°–103° C., after recrystallization from diisopropyl ether, can be converted into the hydrochloride in ethyl acetate by means of gaseous hydrogen chloride; m.p. 198°–202° C., after recrystallization from isopropanol. There is obtained 28.4 g. (62% of theory) 1-(4'-methoxybenzyl)-3-[$N_1$-β-($N_4$-methyl)piperazinoethoxy]-4-phenyl-3-pyrrolin-2-one hydrochloride.

EXAMPLE 11

1-Methyl-3-[$N_1$-β-($N_4$-methyl)-piperazinoethoxy]-4-phenyl-3-pyrrolin-2-one In a manner analogous to that described in Example 2b, 16.8 g. 1-methyl-3-hydroxy-4-phenyl-3-pyrrolin-2-one is reacted with 18.0 g. $N_1$-β-chloroethyl-$N_4$-methylpiperazine. The free base obtained, which melts at 96°–98° C., can be converted into the hydrochloride in ethyl acetate with gaseous hydrogen chloride. After recrystallization from ethanol, this hydrochloride melts at 233°–234° C. There is obtained 9.2 g. (39.6% of theory) 1-methyl-3-[$N_1$-β-($N_4$-methyl)-piperazinoethoxy]-4-phenyl-3-pyrrolin-2-one hydrochloride.

The compounds of formula (I) can be administered orally or parenterally in solid or liquid form. As injection solution, it is preferred to use water which contains the usual additives for injection solutions, such as stabilizing agents, solubilizing agents or buffers. Additives of this kind include, for example, tartrate and citrate buffers, ethanol and complex-forming agents (such as ethylenediaminetetraacetic acid and the non-toxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain additional sweetening and/or flavoring agents.

The enterally administered individual dose is in the range of from about 10 to 200 mg. and the parenteral dose is from about 5 to 50 mg.

Thus, the present invention also provides pharmaceutical compositions containing at least one of the new compounds according to the present invention, in admixture with a solid or liquid pharmaceutical diluent or carrier.

We claim:

1. A compound of the formula:

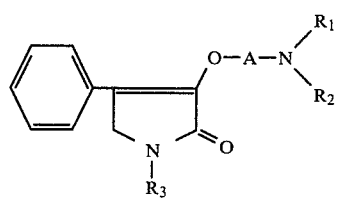

wherein $R_1$ and $R_2$ together with the nitrogen atom to which they are attached form a saturated 5-, 6- or 7-membered heterocyclic ring which can also contain a further nitrogen atom or an oxygen or sulphur atom, A is a straight-chain or branched hydrocarbon chain containing 2 to 4 carbon atoms and $R_3$ is a saturated or unsaturated, straight-chain or branched aliphatic hydrocarbon radical containing up to 6 carbon atoms or is the radical —Alk—Ar, wherein Alk is an alkylene chain containing up to 3 carbon atoms and Ar is a phenyl or heteroaryl radical optionally substituted by halogen atoms and/or lower alkoxy radicals; and the pharmacologically compatible salts thereof.

2. A compound according to claim 1, wherein $R_1$ and $R_2$ together with the nitrogen atom to which they are attached, represent a piperidino, morpholino, piperazino or $N_4'$-methylpiperazino radical, A is an ethylene or propylene chain and $R_3$ is a saturated or unsaturated aliphatic hydrocarbon radical containing up to 4 carbon atoms, Alk is a methylene, ethylene or ethylidene chain and Ar is a phenyl, pyridyl or furyl ring optionally substituted by a chlorine atom or a methoxy radical.

3. The compound according to claim 1 which is 1-Benzyl-3-(β-N-morpholinoethoxy)-4-phenyl-3-pyrrolin-2-one.

4. The compound according to claim 1 which is 1-n-Butyl-3-[$N_1$-β-($N_4$-methyl)-piperazinoethoxy]-4-phenyl-3-pyrrolin-2-one.

5. The compound according to claim 1 which is 1-Ethyl-3-(β-piperidinoethoxy)-4-phenyl-3-pyrrolin-2-one.

6. The compound according to claim 1 which is 1-(4'-Methoxybenzyl)-3-[$N_1$-β-($N_4$-methyl)-piperazinoethoxy]-4-phenyl-3-pyrrolin-2-one.

7. The compound according to claim 1 which is 1-Methyl-3-[$N_1$-β-($N_4$-methyl)-piperazinoethoxy]-4-phenyl-3-pyrrolin-2-one.

8. A pharmaceutical composition comprising an antihypertensive effective amount of at least one compound according to claim 1, in admixture with a solid or liquid pharmaceutical diluent or carrier.

* * * * *